United States Patent
Kim et al.

(10) Patent No.: US 10,890,633 B2
(45) Date of Patent: Jan. 12, 2021

(54) PHASE-DOMAIN DETECTION APPARATUS FOR MIT APPLICATION AND METHOD THEREOF

(71) Applicant: Ulsan National Institute of Science and Technology, Ulsan (KR)

(72) Inventors: Jae Joon Kim, Ulsan (KR); Chansham Park, Ulsan (KR)

(73) Assignee: Ulsan National Institute of Science and Technology, Ulsan (KR)

( * ) Notice: Subject to any disclaimer, the term of this patent is extended or adjusted under 35 U.S.C. 154(b) by 103 days.

(21) Appl. No.: 16/390,344

(22) Filed: Apr. 22, 2019

(65) Prior Publication Data

US 2019/0324100 A1 Oct. 24, 2019

(30) Foreign Application Priority Data

Apr. 24, 2018 (KR) .................. 10-2018-0047433

(51) Int. Cl.
*G01R 33/32* (2006.01)
*A61B 5/05* (2006.01)
*A61B 5/00* (2006.01)
*G01R 33/48* (2006.01)

(52) U.S. Cl.
CPC ............ *G01R 33/32* (2013.01); *A61B 5/0093* (2013.01); *A61B 5/0522* (2013.01); *G01R 33/4812* (2013.01)

(58) Field of Classification Search
CPC .. G01R 33/32; G01R 33/4812; A61B 5/0522; A61B 5/0093
See application file for complete search history.

(56) References Cited

U.S. PATENT DOCUMENTS

| | | | | |
|---|---|---|---|---|
| 8,779,812 | B1 * | 7/2014 | Kavanagh | H03L 7/0891 327/150 |
| 8,786,336 | B1 * | 7/2014 | Schmitt | H03L 7/104 327/156 |
| 9,742,415 | B1 * | 8/2017 | Chegeni | H03L 7/0896 |
| 2012/0319749 | A1 * | 12/2012 | Thaller | H03L 7/183 327/158 |
| 2013/0251084 | A1 * | 9/2013 | Werner | H03L 7/087 375/375 |

(Continued)

OTHER PUBLICATIONS

Shahmohammadi et al., "A Resistor-based Temperature Sensor for MEMS Frequency References," 2013 Proceeding of the ESSCIRC, pp. 225-228, Sep. 2013.

*Primary Examiner* — Dominic E Hawkins
(74) *Attorney, Agent, or Firm* — Foundation Law Group, LLP (57) ABSTRACT

There is provided a phase-domain detection apparatus for MIT application. The phase-domain detection apparatus includes a phase-locked loop unit configured to generate a plurality of reference clock signals having different phases and a phase-domain detection unit. The phase-domain detection unit is configured to receive the reference clock signals from the phase-locked loop unit, receive a response clock signal that is a phase-shifted reference clock signal of a reference clock signal inputted and passed through to a target object among the reference clock signals, and detect a phase difference between the reference clock signal inputted to the target object and the response clock signal.

8 Claims, 4 Drawing Sheets

(56) References Cited

U.S. PATENT DOCUMENTS

| | | | |
|---|---|---|---|
| 2014/0077887 A1* | 3/2014 | Huynh | H03L 7/0891 |
| | | | 331/34 |
| 2016/0036426 A1* | 2/2016 | Grabinski | H03L 7/0802 |
| | | | 327/158 |
| 2018/0064364 A1* | 3/2018 | Oziel | A61B 5/7275 |
| 2019/0004562 A1* | 1/2019 | Gupta | G06F 1/14 |

* cited by examiner

PHASE-DOMAIN DETECTION APPARATUS FOR MIT APPLICATION AND METHOD THEREOF

CROSS-REFERENCE TO RELATED APPLICATIONS

This application claims the benefit of Korean Patent Application No. 10-2018-0047433, filed on Apr. 24, 2018, which is incorporated herein by reference in its entirety.

TECHNICAL FIELD

The present disclosure relates to a phase-domain detection apparatus; and, more particularly, to a phase-domain detection apparatus and method for magnetic induction tomography (MIT) application.

BACKGROUND

Generally, a phase-domain detection apparatus is referred to as an apparatus for detecting a phase difference between two input phase signals.

Figure 1:
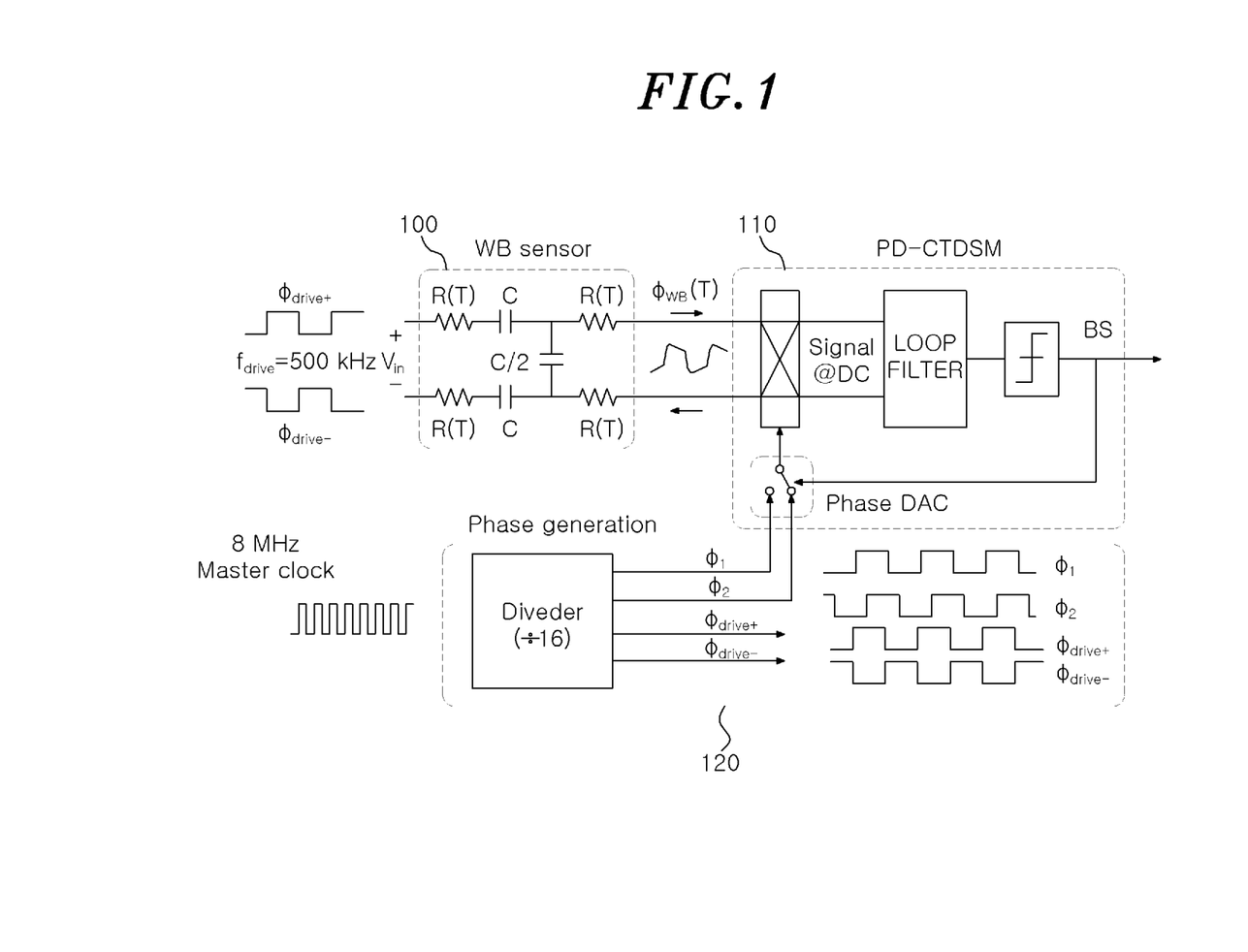
FIG. 1 is a circuit diagram of a resistor-based temperature sensor using a conventional phase-domain detection apparatus.

FIG. 1 is a circuit diagram of a resistor-based temperature sensor using a conventional phase-domain detection apparatus.

Referring to FIG. 1, a Wien bridge sensor (WB sensor) 100 includes resistors R(T) and capacitors C and causes a phase shift of an input signal ($f_{drive}$) due to changes in resistances of the resistors R(T). The WB sensor 100 operates as a bandpass filter, and the resistors R(T) in the sensor 100 are temperature-dependent resistors.

Accordingly, a passband is set differently depending on the changes in the resistances of the resistors, and the phase shift of the input signal ($f_{drive}$) is caused. In other words, the WB sensor 100 outputs phase information of the input signal which has changed in response to the changes in the temperature, and the temperature can be measured by using such phase information.

A phase-domain detection apparatus (PD-CTDSM) 110 obtains phase information in such a way that phase information outputted from the WB sensor 100 is approximated by using a master clock generated by a phase generator 120. Since the phase information includes temperature information, the temperature can be measured by using the phase information.

At this time, the PD-CTDSM 110 requires the master clock for the phase information approximation. Conventionally, it was difficult to generate the master clock because a frequency of the master clock needs to be at least 8 times faster than that of the input signal in order to divide and sense the input signal.

Further, since the frequency of the master clock is considerably faster than that of the input signal, it is difficult for the PD-CTDSM 110 to control the master clock. Accordingly, a detection range of the phase information of the input signal is limited, which results in trade-off between the detection range of the phase information and resolution.

Patent Document: Korean Patent No. 10-1595772 (registered on Feb. 15, 2016)

SUMMARY

In view of the above, the present disclosure provides a phase-domain detection apparatus and method for a phase-domain detection for MIT application, capable of (i) generating a reference clock signal to be applied to an analyzing target object in an internal PPL circuit and (ii) analyzing a phase of a response clock signal, the phase being shifted while the reference clock signal passes through the object, by using reference clock signals having the frequency same as the reference clock signal applied to the analyzing target object from the internal PLL circuit to thereby more accurately detect a phase difference between the reference clock signal applied to the analyzing target object and the response clock signal by preventing mismatch in frequencies of two signals.

In accordance with an aspect of the present disclosure, there is provided a phase-domain detection apparatus for MIT application, including: a phase-locked loop unit configured to generate a plurality of reference clock signals having different phases; and a phase-domain detection unit configured to receive the reference clock signals from the phase-locked loop unit, receive a response clock signal that is a phase-shifted reference clock signal of a reference clock signal inputted and passed through to a target object among the reference clock signals, and detect a phase difference between the reference clock signal inputted to the target object and the response clock signal.

Further, the phase-domain detection unit may include a clock signal selection unit configured to select two or more reference clock signals among the reference clock signals; a phase selection unit configured to select and output one of the two or more reference clock signals whose phase is closer to a phase of the response clock signal; a mixing unit configured to modulate the selected one reference clock signal in the phase selection unit with the response clock signal; and a sigma-delta loop configured to generate bit stream data including information on the phase difference between the selected one reference clock signal and the response clock signal based on the modulated signal outputted from the mixing unit.

Further, the clock signal selection unit may select a first reference clock signal and a second reference clock signal having different phases, and the sigma-delta loop may generate the bit stream data by quantizing phase information between the first reference clock signal and the second reference clock signal by using the modulated signal outputted from the mixing unit.

Further, the sigma-delta loop may include a comparator configured to compare a DC term of the modulated signal with a preset threshold voltage to invert a logic of the DC term when the DC term is greater than or smaller than the preset threshold value, and an integrator configured to filter out a high frequency term of the modulated signal and quantize the phase information between the first reference clock signal and the second reference clock signal selected by the clock signal selection unit by using the modulated signal.

Further, the bit stream data generated by the sigma loop filter may be fed back to the phase selection unit, and the phase selection unit may alternately select one of the first reference clock signal and the second reference clock signal whose phase is closer to the phase of the response clock signal based on the bit stream data and outputs the selected one reference clock signal to the mixing unit.

In accordance with another aspect of the present disclosure, there is provided a phase-domain detection method for MIT application, including: generating a plurality of reference clock signals having different phases; inputting one of the reference clock signals to a target object; receiving a response clock signal that is a phase-shifted reference clock signal of a reference clock signal inputted and passed through to a target object among the reference clock signals;

and detecting a phase difference between the reference clock signal inputted to the target object and the response clock signal.

Further, the step of detecting the phase difference includes selecting a first reference clock signal and a second reference clock signal having different phases among the reference clock signals, selecting one of the first and the second reference clock signal whose phase is closer to a phase of the response clock signal, modulating the selected one reference clock signal with the response clock signal, and generating bit stream data including information on the phase difference between the selected one reference clock signal and the response clock signal based on the modulated signal.

Further, the step of selecting one of the first and the second reference clock signal includes feeding back the bit stream data, and alternately selecting one of the first and the second reference clock signals whose phase is closer to the phase of the response clock signal based on the bit stream data.

In accordance with the aspects of the present disclosure, there is provided the phase-domain detection apparatus for MIT application, which make it possible to more accurately detect the phase difference between the reference clock signal and the response clock signal by (i) generating the reference clock signal to be applied to the object to be analyzed in the internal PLL circuit and (ii) analyzing the phase of the response clock signal which is shifted while passing through the object by using the reference clock signal applied to the object from the internal PLL circuit.

BRIEF DESCRIPTION OF THE DRAWINGS

The objects and features of the present disclosure will become apparent from the following description of embodiments, given in conjunction with the accompanying drawings, in which.

DETAILED DESCRIPTION

Hereinafter, an operation principle of an embodiment of the present disclosure will be described in detail with reference to the accompanying drawings. In the following description of the embodiment of the present disclosure, a detailed description of known functions and configurations incorporated therein will be omitted as it may make the subject matter of the present disclosure unclear. Further, the following terms are defined in consideration of functions used in the present disclosure and may be changed depending on a user's or an operator's intention or practice. Accordingly, the definition thereof should be determined based on the contents throughout the specification.

Figure 2:
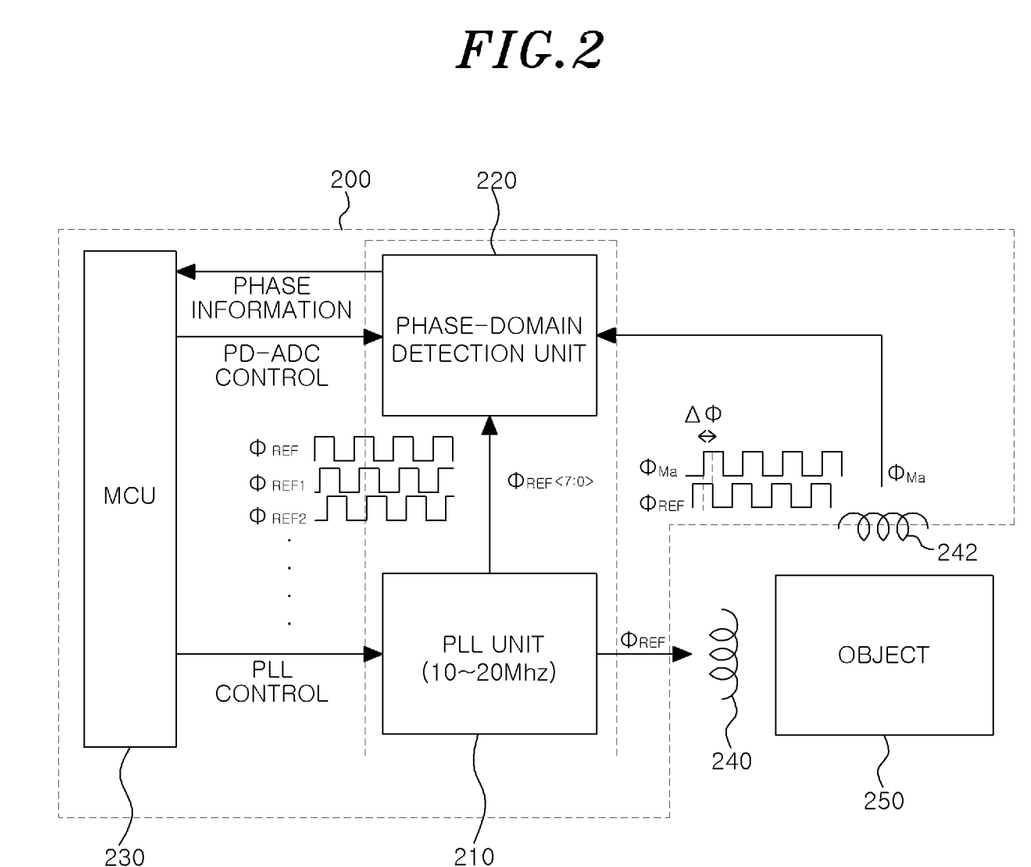
FIG. 2 is a block diagram showing a specific configuration of a phase-domain detection apparatus for MIT application according to an embodiment of the present disclosure.

FIG. 2 is a block diagram showing a specific configuration of a phase-domain detection apparatus 200 for magnetic induction tomography (MIT) application according to an embodiment of the present disclosure.

Hereinafter, operations of components of the phase-domain detection apparatus 200 for MIT application according to the embodiment will be described in detail with reference to FIG. 2.

A phase-locked loop (PLL) unit 210 will be described first. The PLL unit 210 is a circuit that determines a frequency and a phase of a voltage controlled oscillator (VCO) by detecting a phase difference between a reference input signal and an output signal oscillated by the voltage controlled oscillator.

In other words, the PLL unit 210 is a component required for generating an internal clock in the magnetic induction tomography (MIT) system when the MIT system is integrated in a chip. In the embodiment, the PLL unit 210 is configured to generate, e.g., a plurality of reference clock signals φref1 to φref8 having different phases to provide the reference clock signals thus generated to a phase-domain detection unit (PD-ADC) 220. However, the number of the reference clock signals is not limited thereabove.

Specifically, the PLL unit 210 is configured to provide the phase-domain detection unit 220 with the reference clock signals φref1 to φref8 having the same frequency as that of one of the reference clock signals φref1 to φref8 outputted to an object 250, such that there is no frequency mismatch in the phase-domain detection unit 220. Further, in comparison with the conventional case of using an externally generated mask clock, the reference clock signals φref1 to φref8 inputted to the phase-domain detection unit 220 do not require to have excessively high frequency.

Figure 3:
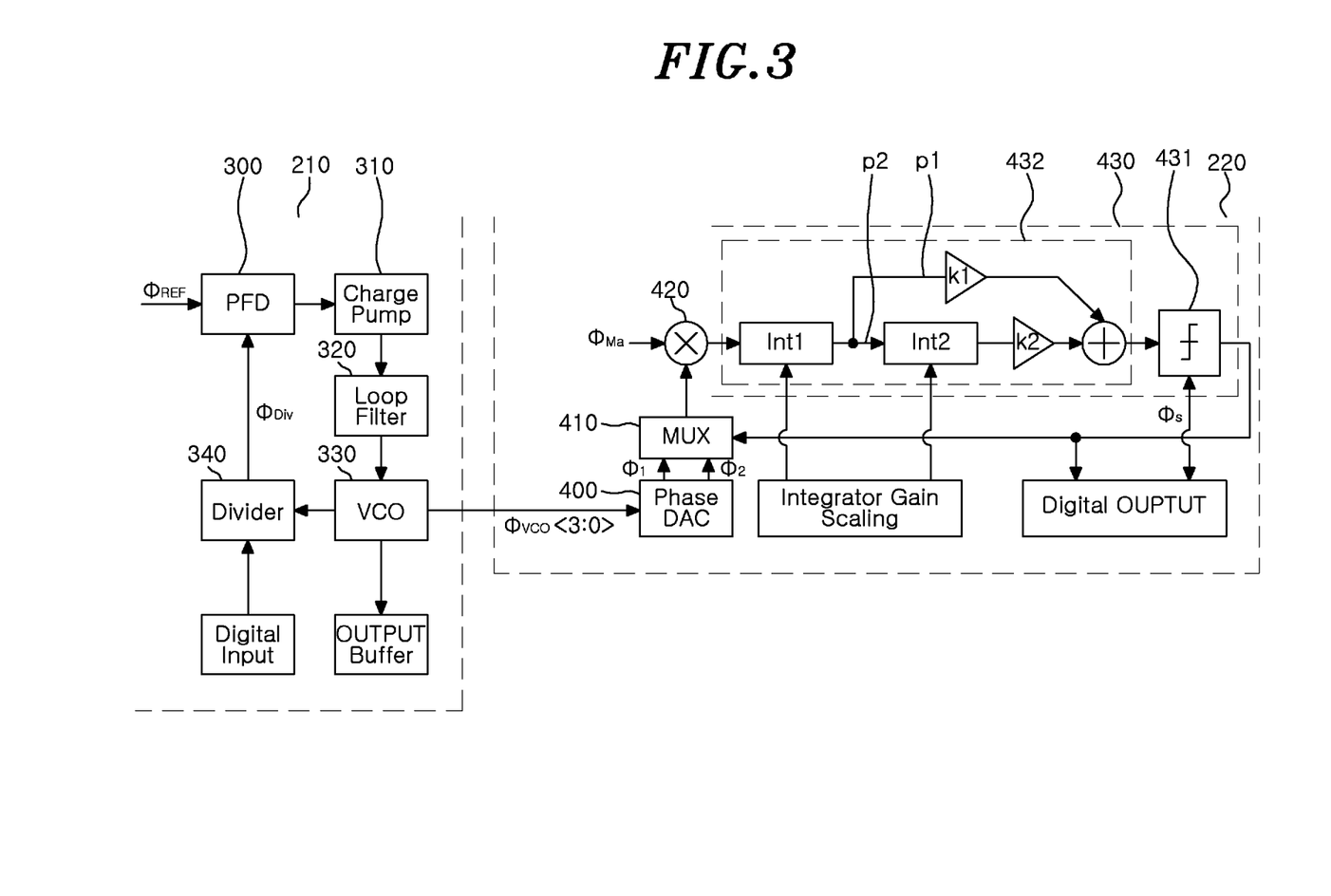
FIG. 3 is a block diagram showing a specific configuration of a PLL unit and a phase-domain detection unit according to the embodiment of the present disclosure.

FIG. 3 is a block diagram showing a specific configuration of the PLL unit 210 and the phase-domain detection unit 220. Hereinafter, operations of components of the PLL unit 210 will be described in detail with reference to FIG. 3.

First, a phase frequency detector (PFD) 300 is configured to detect a phase difference between an input signal inputted thereto and an output signal generated by a voltage controlled oscillator (VCO) 330 and output information on the phase difference.

A charge pump 310 and a loop filter 320 are configured to convert the phase difference detected by the phase frequency detector 300 into a voltage and output the voltage to the voltage controlled oscillator 330.

The voltage controlled oscillator 330 is configured to generate and output an output signal having a frequency proportional to the voltage inputted from the charge pump 310 and the loop filter 320. In the embodiment, the output signal generated by the voltage controlled oscillator 330 serves as each of the reference clock signals φref1 to φref8 inputted to the phase-domain detection unit 220. The phase-domain detection unit 220 to be described later compares phases of the reference clock signals φref1 to φref8 with a phase of a response clock signal φMa that has passed through the object 250.

A divider 340 is configured to divide a frequency of the output signal outputted from the voltage controlled oscillator 330 at a preset ratio and feed the divided frequency back to the phase frequency detector 300.

Next, the phase-domain detection unit 220 will be described in detail. The phase-domain detection unit 220 is configured to receive the reference clock signals φref1 to φref8 outputted from the PLL unit 210 and the response clock signal φMa that is one of the reference clock signals φref1 to φref8 that has passed through the object 250 and detect a phase difference between the reference clock signal applied to the object 250 among the reference clock signals φref1 to φref8 and the response clock signal φMa.

Specifically, one of the reference clock signals φref1 to φref8 generated by the PLL unit 210 is inputted to a first and a second MIT coil 240 and 242. The inputted reference clock signal is converted into an electromagnetic wave signal by the first MIT coil 240, and the electromagnetic wave signal is outputted to the object 250. Then, a phase of the electromagnetic wave signal is shifted due to material characteristic of the object 250 while the electromagnetic wave signal passes through the object 250. The phase-shifted electromagnetic wave signal is outputted to the second MIT coil 242 and converted to the response clock signal φMa by the second MIT coil 242. The response clock signal φMa is outputted to the phase-domain detection unit 220.

In other words, the response clock signal φMa inputted to the phase-domain detection unit 220 denotes the phase-shifted reference clock signal of one of the reference clock signals φref1 to φref8 that is generated by the PLL unit 210 and has shifted its phase while passing through the object 250 due to the characteristics of the object 250. The phase-domain detection unit 220 compares the response clock signal φMa with the reference clock signals φref1 to φref8 that are provided from the PLL unit 210 and have the frequency same as the reference clock signal applied to the object 250 to detect the phase difference between the reference clock signal applied to the object 250 and the response clock signal φMa. Here, the response clock signal φMa and the reference clock signal applied to the object 250 are clock signals generated by the PLL unit 210 while having the same frequency. Therefore, there is no mismatch in frequencies of the signals. Accordingly, the phase difference therebetween can be more accurately detected.

Since the phase difference between the response clock signal φMa and the reference clock signal applied to the object 250 may provide information on the characteristics of the object 250, the information on the phase difference may be used for analyzing the characteristics of the object in the MIT system.

Hereinafter, operations of components of the phase-domain detection unit 220 will be described in detail with reference to FIG. 3.

A clock signal selection unit (Phase DAC) 400 is configured to select two or more reference clock signals having different phases among eight reference clock signals φref1 to φref8 outputted from the PLL unit 210 and output the selected reference clock signals. In the embodiment, two reference clock signals φref1 and φref2 are selected and outputted.

A phase selection unit (MUX) 410 is configured to select one of the two reference clock signals φref1 and φref2 outputted from the clock signal selection unit 400 based on a feedback signal outputted from a sigma-delta loop 430 and output the selected one reference clock signal to a mixing unit 420.

In other words, the two reference clock signals φref1 and φref2 outputted from the clock signal selection unit 400 and the feedback signal outputted from the sigma-delta loop 430 are inputted to the phase selection unit 410.

Then, the phase selection unit 410 selects one of the two reference clock signals φref1 and φref2 outputted from the clock signal selection unit 400 based on the feedback signal to output the selected one reference clock signal.

Here, the feedback signal outputted from the sigma-delta loop 430 may be a DC level signal. When such a DC signal is fed back to the phase selection unit 410, the phase selection unit 410 alternately selects the reference clock signals φref1 and φref2 based on the feedback signal, and the selected reference clock signal is inputted to the mixing unit 420. Therefore, the phase of the response clock signal φMa can be approximated by the sigma-delta loop 430.

The mixing unit, e.g., a chopper 420 is configured to modulate the selected one reference clock signal selected by the phase selection unit 410 with the response clock signal φMa outputted from the object 250.

The sigma-delta loop 430 is configured to receive the modulated signal from the mixing unit 420 and detect the phase difference between the response clock signal φMa and the selected one of the reference clock signals φref1 and φref2 selected by the phase selection unit 410.

In other words, the sigma-delta loop 430 is configured to quantize the phase information between the two reference clock signals φref1 and φref2 by using the modulated signal of the response clock signal φMa and the reference clock signal. The DC level signal is thus generated by such a quantization, and the DC level signal is inputted as a feedback signal into the phase selection unit 410. The DC level signal may include the information on the phase difference between the selected one of the reference clock signals φref1 and φref2 outputted from the phase selection unit 410 and the response clock signal φMa.

For example, when the reference clock signal φref1 having a phase of pi is selected from the phase selection unit 410 and modulated with the response clock signal φMa, the modulated signal outputted from the mixing unit 420 can be expressed as $\cos(wt+\varphi1)*\cos(wt+\varphi Ma)=\cos(\varphi1-\varphi Ma)+\cos(2wt+\varphi1+\varphi Ma)$, which results in generation of a DC term. Here, Cos(2 wt) term, which is a high frequency term of the modulated signal, is filtered out through an integrator 431 provided in the sigma-delta loop 430, and the DC term is fed back in the sigma-delta loop 430. As a consequence, the phase of the response clock signal φMa is approximated.

Hereinafter, an operation in which the phase of the response clock signal φMa is approximated in the sigma-delta loop 430 will be described in detail.

First, the response clock signal φMa that has passed through the object 250 is modulated with one of the reference clock signals φref1 and φref2 respectively having the phase of φ1 and φ2 in the mixing unit 420, so that the DC Term and the AC term thereof are separated and inputted to the sigma-delta loop 430. When the modulated signal, inputted to the sigma-delta loop 430 and passed through a comparator 432 of the sigma-delta loop, has a value greater than or smaller than a threshold voltage, the logic is inverted in the comparator 432 (that is, a low signal is inverted to a high signal, and vice versa).

When the logic is inverted, the logic of the signal inputted to the phase selection unit 410 is inverted, and the phase of the reference clock signal inputted to the mixing unit 420 is inverted. In other words, when the reference clock signal φref1 is previously selected by the phase selection unit 410 and inputted to the mixing unit 420, the reference clock signal φref2 is newly selected and inputted to the mixing unit 420 when the logic is inverted. By repeating this cycle multiple times, it is possible to obtain the phase information that becomes approximated to the phase of the response clock signal φMa.

Next, an operation of a main control unit (MCU) 230 will be described. The MCU 230 is configured to control the overall operations of the PLL unit 210 and the phase-domain detection unit 220.

Specifically, the MCU 230 controls the PLL unit 210 to select a reference clock signal to be applied to the object 250 among the plurality of reference clock signals φref1 to φref8 generated by the PLL unit 210. The selected reference clock signal can be inputted from the PLL unit 210 to the object 250 and the phase-domain detection unit 220.

Further, the MCU 230 may set values of integrator gains int1 and int2 in the sigma-delta loop 430 of the phase region detection unit 220.

Figure 4:
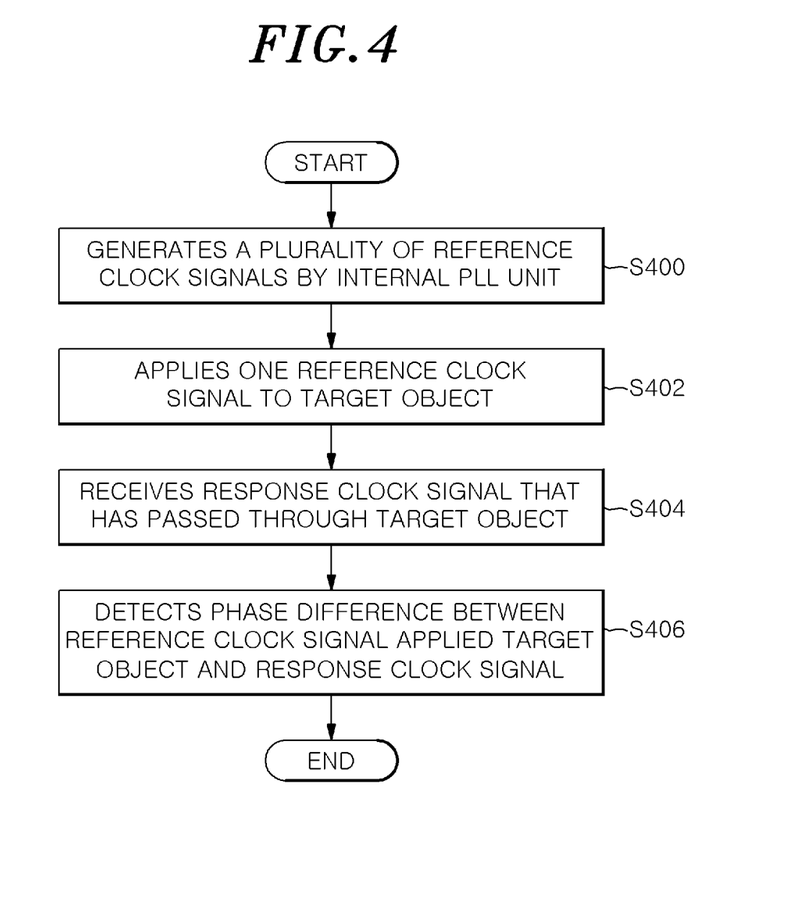
FIG. 4 is a flowchart showing a process of controlling an operation of the phase-domain detection apparatus for application of the MIT according to the embodiment of the present disclosure.

FIG. 4 is a flowchart showing a process of controlling the operation of the phase-domain detection apparatus for MIT application according to the embodiment.

Hereinafter, the operation of the phase-domain detection apparatus will be described in detail with reference to FIGS. 2 to 4.

First, in step S400, the phase-domain detection apparatus 200 generates a plurality of reference clock signals φref1 to φref8 having different phases by the internal PLL unit 210.

Then, in step S402, the phase-domain detection unit 200 applies one of the reference clock signals thus generated to the object (target object) 250. The phase of the reference clock signal applied to the object 250 is shifted while the reference clock signal passes through the object 250.

Then, in step S404, the phase-domain detection apparatus 200 receives a response clock signal φMa that is the phase-shifted reference clock signal obtained after the reference clock signal applied to the object 250 passes through the object 250 and the phase thereof is shifted.

When the response clock signal φMa is inputted to the phase-domain detection apparatus 200, the phase-domain detection apparatus 200 detects, in step S406, the phase difference between the reference clock signal applied to the object 250 and the response clock signal φMa.

Here, since the response clock signal φMa is the phase-shifted reference clock signal obtained after the reference clock signal applied to the object 250 passes through the object 250 and the phase thereof is shifted, the reference clock signal applied to the object 250 and the response clock signal φMa are the clock signals having the same frequency which are generated by the PLL unit 210 in the phase-domain detection apparatus 200. Therefore, there is no mismatch in the frequencies of the signals, which makes it possible to more accurately detect the phase difference.

As described above, in accordance with the embodiment of the present disclosure, there is provided the phase-domain detection apparatus for MIT application, which make it possible to more accurately detect the phase difference between the reference clock signal to be applied to an analyzing target object and the response clock signal by (i) generating the reference clock signal to be applied to the analyzing target object in the internal PLL circuit and (ii) analyzing the phase of the response clock signal, the phase being shifted while the reference clock signal passes through the object, by using reference clock signals having the frequency same as the reference clock signal to be applied to the analyzing target object from the internal PLL circuit.

Combinations of blocks in the flowcharts of the present disclosure can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the steps of the flowchart. These computer program instructions may also be stored in a computer usable or computer readable memory that can direct a computer or other programmable data processing apparatuses to function in a particular manner, such that the instructions stored in the computer usable or computer readable medium can produce an article of manufacture including instructions which implement the function specified in the blocks of the flowcharts. The computer program instructions may also be loaded onto a computer or other programmable data processing apparatuses to cause a series of operational steps to be performed on the computer or other programmable apparatuses to produce a computer implemented process such that the instructions which execute on the computer or other programmable apparatuses provide processes for implementing the functions specified in the blocks of the flowcharts.

Each block in the flowchart may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

While the present disclosure has been shown and described with respect to the embodiments, it will be understood by those skilled in the art that various changes and modifications may be made without departing from the scope of the present disclosure as defined in the following claims.

What is claimed is:

1. A phase-domain detection apparatus for MIT application, comprising:
a phase-locked loop unit configured to generate a plurality of reference clock signals having different phases; and
a phase-domain detection unit configured to receive the reference clock signals from the phase-locked loop unit, receive a response clock signal that is a phase-shifted reference clock signal of a reference clock signal inputted to and passed through a target object among the reference clock signals, and detect a phase difference between the reference clock signal inputted to the target object and the response clock signal.

2. The phase-domain detection apparatus for MIT application of claim 1, wherein the phase-domain detection unit includes:
a clock signal selection unit configured to select two or more reference clock signals among the reference clock signals;
a phase selection unit configured to select and output one of the two or more reference clock signals whose phase is closer to a phase of the response clock signal;
a mixing unit configured to modulate the selected one reference clock signal by the phase selection unit with the response clock signal; and
a sigma-delta loop configured to generate bit stream data including information on the phase difference between the selected one reference clock signal and the response clock signal based on the modulated signal outputted from the mixing unit.

3. The phase-domain detection apparatus for MIT application of claim 2, wherein the clock signal selection unit selects a first reference clock signal and a second reference clock signal having different phases, and the sigma-delta loop generates the bit stream data by quantizing phase information between the first reference clock signal and the second reference clock signal by using the modulated signal outputted from the mixing unit.

4. The phase-domain detection apparatus for MIT application of claim 3, wherein the sigma-delta loop includes:
  a comparator configured to compare a DC term of the modulated signal with a preset threshold voltage to invert a logic of the DC term when the DC term is greater than or smaller than the preset threshold value; and
  an integrator configured to filter out a high frequency term of the modulated signal and quantize the phase information between the first reference clock signal and the second reference clock signal selected by the clock signal selection unit by using the modulated signal.

5. The phase-domain detection apparatus for MIT application of claim 3, wherein the bit stream data generated by the sigma loop filter is fed back to the phase selection unit, and
  wherein the phase selection unit alternately selects one of the first reference clock signal and the second reference clock signal whose phase is closer to the phase of the response clock signal based on the bit stream data and outputs the selected one reference clock signal to the mixing unit.

6. A phase-domain detection method for MIT application, comprising:
  generating a plurality of reference clock signals having different phases;
  inputting one of the reference clock signals to a target object;
  receiving a response clock signal that is a phase-shifted reference clock signal of a reference clock signal inputted to and passed through a target object among the reference clock signals; and
  detecting a phase difference between the reference clock signal inputted to the target object and the response clock signal.

7. The phase-domain detection method for MIT application of claim 6, wherein said detecting the phase difference includes:
  selecting a first reference clock signal and a second reference clock signal having different phases among the reference clock signals;
  selecting one of the first and the second reference clock signal whose phase is closer to a phase of the response clock signal;
  modulating the selected one reference clock signal with the response clock signal; and
  generating bit stream data including information on the phase difference between the selected one reference clock signal and the response clock signal based on the modulated signal.

8. The phase-domain detection method for MIT application of claim 7, wherein said selecting one of the first and the second reference clock signal includes:
  feeding back the bit stream data; and
  alternately selecting one of the first and the second reference clock signals whose phase is closer to the phase of the response clock signal based on the bit stream data.

* * * * *